United States Patent [19]

Christy

[11] Patent Number: 5,639,956
[45] Date of Patent: Jun. 17, 1997

[54] PERMEABLE MEMBRANE SOIL PROBE

[75] Inventor: Thomas M. Christy, Salina, Kans.

[73] Assignee: Kejr Engineering, Inc., Salina, Kans.

[21] Appl. No.: 561,919

[22] Filed: Nov. 22, 1995

[51] Int. Cl.$^6$ ................................................ G01N 33/18
[52] U.S. Cl. ............................. 73/19.01; 73/863.23
[58] Field of Search ............................. 73/863, 863.21,
73/863.23, 23.21, 19.1

[56] References Cited

U.S. PATENT DOCUMENTS

| | | | |
|---|---|---|---|
| 3,673,864 | 7/1972 | Cubberly, Jr. | 73/863.23 |
| 3,913,384 | 10/1975 | Furuya et al. | 73/19.1 |
| 5,035,149 | 7/1991 | Wierenga | 73/863.23 |
| 5,147,561 | 9/1992 | Burge et al. | 73/19.1 |
| 5,330,720 | 7/1994 | Sorbo et al. | 73/40 |

OTHER PUBLICATIONS

Pp. 3.1 to 5.1 of "Geoprobe Systems 1993–94 Equipment and Tools Catalog" which was published prior to Nov. 22, 1994.

*Primary Examiner*—Richard Chilcot
*Assistant Examiner*—Max H. Noori
*Attorney, Agent, or Firm*—Shook, Hardy & Bacon L.L.P.

[57] ABSTRACT

A permeable membrane sensor probe has a housing with a gas permeable membrane. The membrane has an outer surface and an inner surface. The membrane outer surface is disposed adjacent an outer soil engaging surface of the housing. The membrane is adapted to allow the gas phase of at least one particular chemical compound found in the soil to permeate through the membrane from the membrane outer surface to the membrane inner surface while substantially preventing the transfer of liquids and solids found in the soil through the membrane. A gas detecting arrangement is disposed adjacent the membrane inner surface and inside of the housing. This detection system detects the presence of a particular compound at different soil levels.

17 Claims, 1 Drawing Sheet

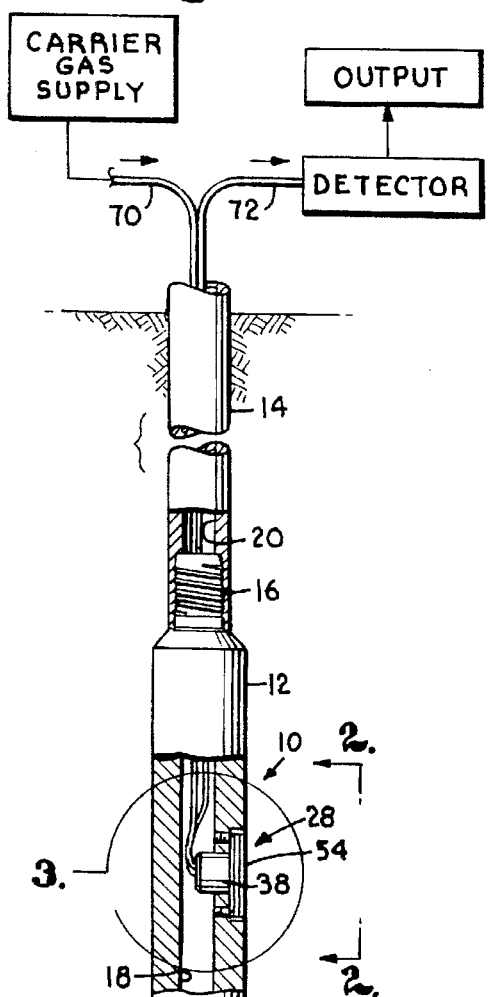
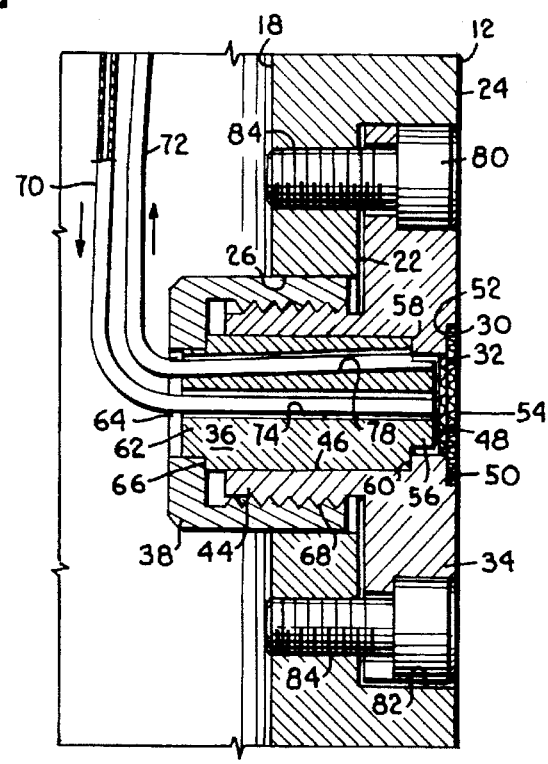
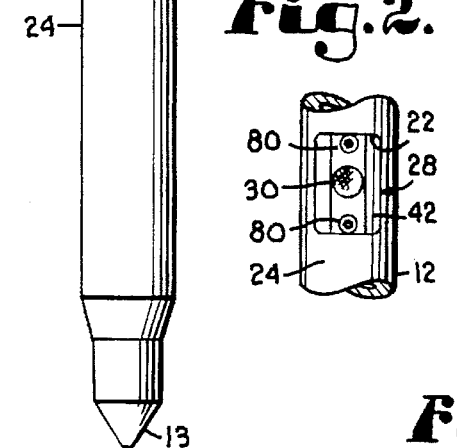
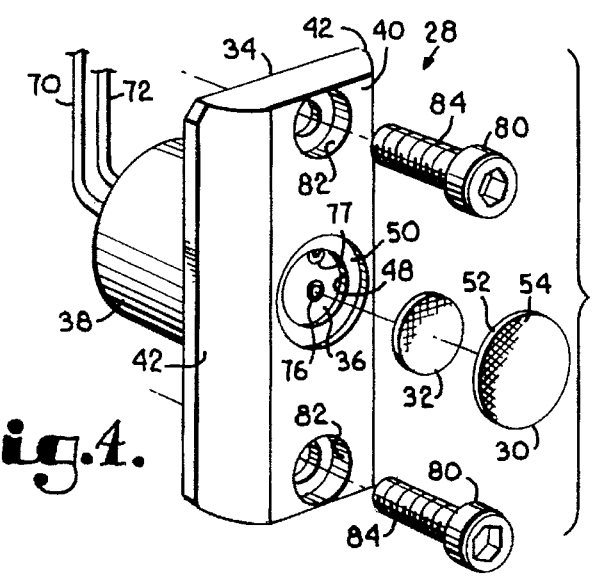

PERMEABLE MEMBRANE SOIL PROBE

This invention relates to a soil probe which is driven into the ground, and, more particularly, to a soil probe for sensing and/or measuring naturally occurring compounds and/or foreign contaminants in soil or ground water.

In recent years, small diameter soil probing tools have been increasingly used for subsurface investigations. These tools are typically driven into the ground using percussion hammers and are primarily used for sampling soil vapor, soil cores, or ground water. With the increasing usage of these probing tools, improvements have been made in the tools and the driving mechanisms such that the depth of investigation at which the probing tools are used is gradually increased. One use of such probing tools has been the exploration of a site for naturally occurring compounds or foreign contaminants in the soil and ground water of the site. The investigation of such a site, however, involves a very labor intensive and time consuming operation. More specifically, to determine whether particular compounds or contaminants are present at a particular soil level, an actual soil or ground water sample is taken at that level. To perform such sampling, a special probe is positioned on the lower end of a probe rod string and driven into the ground to the particular level at which a sample is to be taken. The probe is actuated in some manner to allow collection of actual soil or ground water found at that level. The probe rod string is then removed from the ground to retrieve the probe and soil sample therein. Thereafter, the soil sample or ground water sample is removed from the probe and analyzed using various detection and quantifying instruments. As is apparent, if it is desirable to investigate a site to determine the presence and/or quantity of certain compounds or contaminants at a variety of different levels, the use of this direct soil/ground water sampling operation can involve a substantial amount of labor and time. More specifically, to detect compounds or contaminants at various levels the probe rod string must be driven to each particular level, a sample taken, and thereafter the sample removed from the ground by removing the probe rod string. Thus, numerous iterations of driving the probe rod string into the ground and then retracting the probe rod string from the ground are required to sample the various soil levels.

Therefore, a probe capable of detecting and quantifying chemical compounds and contaminants at particular soil levels is needed which overcomes the disadvantages and shortcomings of the prior art probes discussed above. Furthermore, many of the chemical compounds and contaminants of interest in the subsurface are volatile compounds which either exist wholly in the gas phase at normal soil temperatures, or exhibit a substantial vapor pressure while existing in the soil in the dissolved, liquid, or solid phases. Many of these compounds, in addition to being volatile, will also rapidly diffuse through many solid materials.

Accordingly, it is a primary object of the present invention to allow detection of certain compounds at a subsurface level without bringing a soil sample or ground water sample to the surface.

A further important object of the present invention is to provide a probe that can detect contaminants in both saturated and unsaturated soil zones, the probe having a membrane that allows diffusion of chemical compounds in their gas phase into the probe.

Another object of the present invention is to provide a probe construction with a permeable membrane that is resistant to tearing and collapsing as the probe is driven through the soil and the membrane is exposed to the soil.

A still further object of the present invention is to provide a probe construction that conveys gas phase compounds which diffuse across the permeable membrane at certain subsurface soil levels to the surface for detection and evaluation.

These and other important aims and objectives of the present invention will be further described, or will become apparent from the following description and explanation of the drawings, wherein:

FIG. 1 is a side elevational view of a permeable membrane probe embodying the principles of this invention and showing the probe positioned on the lower end of a probe rod string being driven into the ground, parts being broken away and shown in cross section to reveal details of construction;

FIG. 2 is a fragmentary front elevational view of the probe shown in FIG. 1 taken generally along lines 2—2 and showing the permeable membrane unit attached to the probe housing;

FIG. 3 is an enlarged view of the area designated by the numeral 3 in FIG. 1, the flow of carrier gas indicated by the arrows; and FIG. 4 is an exploded perspective view of the permeable membrane unit not attached to the probe housing.

A permeable membrane probe involving the principles of this invention is broadly designated in the drawings by the reference numeral 10. Probe 10 has a cylindrical housing 12 which is adapted to be positioned on the lower end of a probe rod string 14 by a thread arrangement 16 as best shown in FIG. 1. Housing 12 has a lower conical drive point 13 for parting the soil as the probe is driven into the ground. Housing 12 has a central bore 18 which is aligned with a central bore 20 of probe rod string 14. Rod string 14 includes a plurality of probe rod segments which can be interconnected to one another as the probe is driven into the ground, as will be more fully described below.

Housing 12 has a generally rectangular recess 22 formed on its outer peripheral surface 24 as best shown in FIGS. 2 and 3. A through aperture 26 extends between and spatially connects bore 18 and recess 22. Recess 22 and aperture 26 receive a sensing unit 28.

Sensing unit 28 includes a permeable membrane 30, a gas distribution screen 32, a holding member 34, a cylindrical reinforcing plug 36, and a plug retaining cap 38 as best shown in FIGS. 3 and 4. Holder 34 has a generally rectangular configuration to conform with recess 22. The outer surface of holder 34 has a centrally disposed flat portion 40 and generally curved side portions 42 as best shown in FIGS. 2 and 4. Curved portions 42 generally follow the curvature of the peripheral surface 24 of housing 12 to reduce the soil buildup around unit 28 as the probe is driven into the ground. Holder 34 further includes a threaded nipple 44, which partially forms a bore 46, extending from the distal end of the nipple all the way through holder 34 to front flat portion 40 of holder 34. Bore 46 has a reduced diameter portion 48 and an annular recess 50, which opens up to flat portion 40. Recess 50 has a larger overall diameter than bore 46, and is used to receive membrane 30 as best shown in FIGS. 3 and 4.

Membrane 30 is formed of a circular disc of stainless steel screen which has been coated with a polymer. The polymer is applied in a manner well known in the art such that the openings of the screen are filled, thus making the screen impervious to the bulk flow of either gases, liquids or solids. However, the polymer itself is actually porous, and is permeable to the diffusion of certain compounds which may be present in the soil surrounding the probe. Many different types of polymers could be used for the screen coating, depending on the type of compound to be detected in the surrounding soil. More specifically, polymers vary greatly in their permeability to gaseous diffusion. Thus, a particular polymer can be chosen which will allow diffusion of a particular compound to be detected from the soil surrounding the probe. It has been found that a TFE polymer manufactured by E. I. Du Pont de Nemours & Co. of Wilmington, Del., is a preferable type of polymer to be used to coat the screen. This polymer is baked onto the screen in successive layers, and allows maximum diffusion and minimum sorption of contaminant compounds found in the soil. However, as indicated above, other polymers could be used which have different permeability attributes. For instance, a polymer could be chosen which will admit polar compounds to the exclusion of nonpolar compounds. Membrane 30 can be secured in annular recess 50 by resistance welding, brazing, or any other suitable means of attaching the membrane to holder 34.

The mass of a compound passing through the membrane can also be regulated or adjusted by varying the size and thickness of the membrane. More specifically, presently a membrane having an area of 0.058 square inches and a thickness of 0.030 inches is used. To increase the mass transfer of a compound across the membrane, the surface area of the membrane could be increased.

Gas distribution screen 32 is positioned adjacent an inner surface 52 of membrane 30 and within reduced diameter portion 48 of bore 46 as shown in FIGS. 3 and 4. The interstices of screen 32 form a gas mixing area wherein gas that has permeated through membrane 30 from the surrounding soil can be picked up by a carrier gas circulated within the mixing area, as will be more fully described below. Further, screen 32 supports membrane 30 to prevent the inward collapsing of the membrane due to soil pressure exerted on the outer surface 54 of the membrane, also as will be more fully described below.

Plug 36 is positioned within bore 46 and serves to prevent inward collapsing of membrane 30 due to soil pressure. Plug 36 has a generally cylindrical nose portion 56 which is partially disposed in portion 48 and abuts against the inner surface of screen 32 as shown in FIG. 3. Plug 36 also has an annular shoulder 58 which engages an annular ridge 60 formed where bore 46 transitions to reduce diameter portion 48. The inner end of plug 36 also has a protruding portion 62 which extends into an aperture 64 formed in the end of cap 38 as best shown in FIG. 3. An annular shoulder 66 of plug 36 engages the inner surface of cap 38 adjacent aperture 64 to hold plug 36 within bore 46. Cap 38 is secured to nipple 44 through thread arrangement 68.

Cap 38, plug 36 and screen 32 all serve the advantageous function of preventing inward collapsing of membrane 30 due to pressure exerted on its outer surface 54 by the soil through which the probe passes. More specifically, plug 36 is securely positioned within bore 46 by cap 38 and supports the inner surface of screen 32. Screen 32 in turn supports the inner surface 52 of membrane 30 to prevent inward movement. Additionally, the interstices of screen 32 allow gas that has permeated through the membrane to be picked up by the carrier gas circulated through the interstices and then returned to the surface for analyzing, as will be described. Screen 32 is preferably a rigid stainless steel mesh screen. However, screen 32 can be comprised of other materials, such as porous sintered stainless steels, so long as the material used for the screen can transfer support force from plug 36 to membrane 30 and allow for free flow of carrier gas between the membrane and the plug.

A carrier gas is used to convey the gas which has permeated through the membrane upwardly to the surface and into a suitable analyzing detecting instrument as generally shown in FIG. 1. As discussed above, the carrier gas mixes with the permeated gas within a gas mixing area formed by the interstices of screen 32. Carrier gas is conveyed to this gas collection area via a flexible inlet tube 70 as shown in FIGS. 1 and 3. Carrier gas and the mixed permeated gas are returned to the surface via a flexible return tube 72. Tubes 70 and 72 extend from unit 28 through the bore 18 of housing 12, upwardly through the connected bores 20 of the probe rod string 14, and out the upper end of the probe rod string. Inlet tube 70 is connected at its upper end to a supply of carrier gas as shown in FIG. 1. The carrier gas is preferably an inert gas, such as nitrogen or helium. The lower end of inlet tube 70 extends through an inlet bore 74 formed in plug 36. The extreme lower open end 76 of tube 70 is positioned adjacent screen 32 to supply carrier gas to the mixing area formed by screen 32 as best shown in FIGS. 3 and 4. The lower end of return tube 72 is positioned in a return bore 78, also formed in plug 36. Tube 72 has an open end 77 disposed adjacent screen 32 to collect carrier gas mixed with the permeated gas and return this mixture to the surface as best shown in FIGS. 3 and 4. The end of tube 72 and the end of bore 78 adjacent screen 32 are formed in a generally half-moon shape to allow collection of the mixture of carrier gas and permeated gas. The upper end of tube 72 is connected to a suitable gas analyzer, which can determine the presence and/or quantity of particular types of gases.

Sensing unit 28 is removably secured to housing 12 via fastening screws 80 positioned in counter-sunk holes 82 of holder 34 and holes 84 of housing 12 as best shown in FIGS. 3 and 4.

In operation, probe 10, with sensing unit 28 attached thereto, is positioned on the lower end of a probe rod string and driven into the ground using a hydraulically driven percussion hammer (not shown). As the probe is driven into the ground, clean carrier gas is supplied from a carrier gas supply source to sensing unit 28 via tube 70. The carrier gas continuously flows within the interstices of screen 32 adjacent inner surface 52 of membrane 30. Certain volatile compounds found within the soil the probe is passing through permeate through membrane 30 and into the mixing area formed by the interstices of screen 32. In this mixing area, carrier gas is mixed with the permeated gas and flows upwardly and into return tube 72. The carrier gas and permeated gas are conveyed upwardly through tube 72 to a detector device located on the surface of the ground.

Various different analyzing devices can be utilized for this return flow of carrier gas and permeated gas to detect and/or quantify the permeated gas. For instance, the return flow can be directed to a flame ionization detector which is commonly used for sensing hydrocarbons. Further, other detection devices may also be used in parallel with the flame ionization detector. Such devices could include carbon dioxide, oxygen, or humidity sensors. The returning carrier gas could also be directed to a mass spectrometry detector or, indeed, any device for the measurement of compounds in the gas phase. A typical data output from use of the arrangement shown in FIG. 1 will show increased detector response at depths where increased levels of a particular compound are encountered in the subsurface. More specifically, detections of particular compounds can be measured with respect to time as the probe is driven into the ground. Further, the depth of the probe with respect to time can also be measured using means well known in the art. Thereafter, the two sets of data can be correlated so that a reading of detection of compounds with respect to depth can be obtained. Further, it may be possible to measure the detection signal with respect to depth directly using a depth-measuring system that is well known in the art, for instance, a string pot system. As is apparent, the preferred depiction of the data gathered by this device is in a graph format wherein time or depth is marked on one axis and detection levels are marked on the other axis.

As is further apparent, there is a time lag in detecting compounds in the soil when using the detection system of this invention. More specifically, this time lag arises from the time required for a compound to pass through the membrane and then be conveyed to the ground surface in the carrier gas stream. The time lag is primarily determined by the diffusion coefficient of the compound encountered, the thickness and gas permeability of the membrane, the temperature of the soil, the rate of carrier gas flow, and the length of the gas tubes. All these factors are taken into account when analyzing the time and depth data from the various instruments.

A major advantage of the probe of the present invention over equipment presently used in subsurface investigation is that levels or areas of contamination can be found without actually bringing a sample of either soil or ground water to the surface. Because probe 10 does not allow for the bulk flow of either water, solids or gas across membrane 30, probe 10 can be used both in unsaturated zones of soil where the voids of the soil are filled with gas or in saturated zones of soil where void spaces are filled with ground water. Compounds which exist in the soil atmosphere in phases other than the gas phase (e.g., liquid or solid phases) can be detected by probe 10. Such compounds will partition into the gas phase adjacent the outer membrane surface and diffuse through the membrane into the carrier gas. Various compounds could potentially be detected using probe 10 depending upon the type of polymer used in membrane 30. These compounds typically will exhibit a vapor pressure at ambient temperature. The types of compounds that may be detected include aliphatic hydrocarbons such as butane, propane, ethane or pentane; aromatic hydrocarbons such as benzene or toluene; chlorinated hydrocarbons such as trichloroethylene, chloroform, tetrachloroethylene, or 1,1,1-trichlorethane; permanent gases such as carbon dioxide or oxygen; and water.

Another advantageous feature of probe 10 is the supporting of membrane 30 by plug 36 and screen 32. More specifically, as the probe is driven into the ground, soil pressure is exerted on outer surface 54 of membrane 30. This soil pressure will attempt to deform membrane 30 inwardly. The positioning of support plug 36 within bore 46 and the holding of the plug therein by cap 38 serves to provide a firm support surface to prevent inner movement of membrane 30. Further, rigid screen 32 acts to transfer the support of plug 36 to inner surface 52 of the membrane while at the same time allowing the mixing of permeated gas and carrier gas. Further, it has been found to be advantageous to have outer surface 54 of membrane 30 generally flush with peripheral surface 24 of housing 12, as best shown in FIG. 3. This positioning allows the membrane surface to be self-cleaning. In other words, soil encountered at one depth is not carried with the probe to the next depth, but rather is sheared off and replaced with new soil from the next depth increment. Therefore, it is ensured that the compounds sampled by the probe are those found in the soil at the level the probe is at as opposed to soil that has been carried along with the probe during driving.

As an alternative to circulating carrier gas along the inner surface of the membrane, a chemical sensor can be positioned directly within the probe adjacent the inner surface of the membrane. The sensor can sense directly the presence of a particular type of compound that has permeated through the membrane and relays such information to the surface electrically through wires or photometrically through optical fibers disposed in the central bores of the probe rod string and housing. Such a sensor could possibly take the place and be configured to be the same shape as plug 36. The advantage of placing the chemical sensor in the probe is that the time lag of conveying a carrier gas to the surface for analysis is eliminated, as is the need for a carrier gas supply system.

I claim:

1. A permeable membrane sensor probe adapted to be driven into the ground at the lower end of a string of probe rods, comprising:

a housing having a gas permeable membrane with an outer surface, an inner surface and a rigid screen, said membrane outer surface disposed adjacent an outer soil engaging surface of said housing, said rigid screen being coated with a polymer, said polymer allowing the gas phase of at least one particular chemical compound found in the soil to permeate through said membrane from said membrane outer surface to said membrane inner surface while substantially preventing the transfer of liquid and solids found in said soil through said membrane; and means disposed adjacent said inner membrane surface and inside of said housing for detecting the presence of the compound at different soil levels.

2. The permeable membrane probe of claim 1 wherein said outer membrane surface directly engages the soil.

3. The permeable membrane probe of claim 1 wherein said membrane is generally circular in shape and is oriented generally parallel to the direction of travel of said probe.

4. The permeable membrane probe of claim 1 further comprising a support plug positioned adjacent said membrane inner surface and within an opening formed in said housing, said support plug secured to said housing so that said membrane is supported and prevented from collapsing inwardly due to pressure from the soil.

5. The permeable membrane probe of claim 4 further comprising a means for forming a gas mixing area wherein gas that has permeated through said membrane can mix with carrier gas flowing through said area, said gas mixing area means disposed between said plug and said membrane inner surface.

6. The permeable membrane probe of claim 5 wherein said gas mixing area means is a rigid screen.

7. A permeable membrane sensor probe adapted to be driven into the ground at the lower end of a string of probe rods, comprising:

a generally cylindrical housing having a gas permeable membrane with an outer surface and an inner surface, said membrane outer surface disposed adjacent an outer soil engaging surface of said housing so that said membrane outer surface is substantially flush with an outer peripheral soil engaging surface of said housing, said membrane adapted to allow the gas phase of at least one particular chemical compound found in the soil to permeate through said membrane from said membrane outer surface to said membrane inner surface while substantially preventing the transfer of liquid and solids found in said soil through said membrane; and means disposed adjacent said inner membrane surface and inside of said housing for detecting the presence of the compound at different soil levels.

8. The permeable membrane probe of claim 7 further comprising a support plug positioned adjacent said membrane inner surface and within an opening formed in said housing, said support plug secured to said housing so that said membrane is supported and prevented from collapsing inwardly due to pressure from the soil.

9. The permeable membrane probe of claim 8 further comprising a means for forming a gas mixing area wherein gas that has permeated through said membrane can mix with carrier gas flowing through said area, said gas mixing area means disposed between said plug and said membrane inner surface.

10. The permeable membrane probe of claim 9 wherein said gas mixing area means is a rigid screen.

11. A permeable membrane sensor probe adapted to be driven into the ground at the lower end of a string of probe rods, comprising:

a housing having a gas permeable membrane with an outer surface and an inner surface, said membrane outer surface disposed adjacent an outer soil engaging surface of said housing, said membrane adapted to allow the gas phase of at least one particular chemical compound found in the soil to permeate through said membrane from said membrane outer surface to said membrane inner surface while substantially preventing the transfer of liquid and solids found in said soil through said membrane;

means disposed adjacent said inner membrane surface and inside of said housing for detecting the presence of the compound at different soil levels, said detecting means including means for circulating a carrier gas adjacent to said membrane inner surface, said circulating means including a supply tube for supplying said carrier gas adjacent to said membrane inner surface and a return tube for conveying carrier gas with permeated gas to an instrumentation device; and means for forming a gas mixing area wherein gas that has permeated through said membrane can mix with carrier gas prior to being detected, said gas mixing area means positioned adjacent said membrane inner surface, said supply tube and said return tube opening at their lower ends to said gas mixing area means.

12. The permeable membrane probe of claim 11 further including a support plug positioned adjacent said gas mixing area means and within an opening formed in said housing, said support plug secured to said housing so that said membrane is supported and prevented from collapsing inwardly due to pressure from the soil, said supply tube and said return tube disposed in corresponding bores formed in said plug.

13. The permeable membrane probe of claim 12 further comprising a membrane holding member removably secured to said housing, said holding member holding said membrane, said gas mixing area means, and said plug.

14. A permeable membrane probe adapted to be driven into the ground at the lower end of a string of probe rods, comprising:

a housing having a gas permeable membrane with an outer surface and an inner surface, said membrane outer surface disposed adjacent an outer ground engaging surface of said housing, said membrane adapted to allow the gas phase of at least one particular chemical compound found in said soil to permeate through said membrane from said membrane outer surface to said membrane inner surface while substantially preventing the transfer of liquids and solids found in said soil through said membrane;

a supply tube adapted to supplying a carrier gas to a location adjacent to said membrane inner surface;

a return tube adapted to convey the carrier gas and gas that has permeated through said membrane to a detection instrument;

a rigid screen positioned adjacent the membrane inner surface, said screen forming a gas mixing area where carrier gas from said supply tube can mix with gas that has permeated through said membrane; and a support plug positioned in an opening formed in said housing and secured to said housing, said rigid screen positioned between said membrane inner surface and said plug so that said membrane is prevented from collapsing inwardly due to soil pressure.

15. The permeable membrane probe of claim 14 wherein said outer membrane surface directly engages said soil.

16. The permeable membrane probe of claim 15 wherein said housing is generally cylindrical in shape and said membrane outer surface is substantially flush with an outer peripheral soil engaging surface of said housing.

17. The permeable membrane probe of claim 16 wherein said membrane is generally circular in shape and is oriented generally parallel to the direction of travel of said probe.

* * * * *